(12) United States Patent
Eberhardt et al.

(10) Patent No.: US 8,063,239 B2
(45) Date of Patent: Nov. 22, 2011

(54) PROCESS FOR PREPARING AMINOALKYLNITRILES AND DIAMINES FROM SUCH NITRILES

(75) Inventors: Jan Eberhardt, Mannheim (DE); Thilo Hahn, Kirchheimbolanden (DE); Johann-Peter Melder, Böhl-Iggelheim (DE); Gerhard Fritz, Dannstadt-Schauernheim (DE); Volkmar Menger, Neustadt (DE); Thomas Hill, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 385 days.

(21) Appl. No.: 12/298,939

(22) PCT Filed: May 7, 2007

(86) PCT No.: PCT/EP2007/054381
§ 371 (c)(1),
(2), (4) Date: Oct. 29, 2008

(87) PCT Pub. No.: WO2007/128803
PCT Pub. Date: Nov. 15, 2007

(65) Prior Publication Data
US 2009/0069590 A1    Mar. 12, 2009

(30) Foreign Application Priority Data
May 9, 2006 (EP) .................................. 06113718

(51) Int. Cl.
*C07F 7/00* (2006.01)
(52) U.S. Cl. ....................................... 558/452; 564/490
(58) Field of Classification Search .................. 558/452; 564/490
See application file for complete search history.

(56) References Cited

U.S. PATENT DOCUMENTS

| | | | |
|---|---|---|---|
| 4,172,091 A | 10/1979 | Weber et al. | |
| 4,965,362 A | 10/1990 | Merger et al. | |
| 5,530,127 A | 6/1996 | Reif et al. | |
| 5,675,045 A | 10/1997 | Bueschken et al. | |
| 5,696,048 A | 12/1997 | Breitscheidel et al. | |
| 6,281,388 B1 * | 8/2001 | Goodwin et al. | 564/492 |
| 6,297,394 B1 | 10/2001 | Voit et al. | |
| 6,790,995 B2 | 9/2004 | Pfeffinger et al. | |
| 6,790,996 B2 | 9/2004 | Ansmann et al. | |
| 7,723,547 B2 * | 5/2010 | Ernst et al. | 564/490 |

FOREIGN PATENT DOCUMENTS

| | | |
|---|---|---|
| DE | 58306 | 11/1966 |
| DE | 2709966 | 8/1978 |
| DE | 222011 | 5/1985 |
| DE | 19524971 | 1/1997 |
| DE | 102005052457 | 5/2007 |
| EP | 089 277 | 9/1983 |
| EP | 0352504 | 1/1990 |
| EP | 696 572 | 2/1996 |
| EP | 742 045 | 11/1996 |
| EP | 963 975 | 12/1999 |
| EP | 1221437 | 7/2002 |
| EP | 1306365 | 5/2003 |
| WO | WO 99/44984 | 9/1999 |

* cited by examiner

*Primary Examiner* — Rei-tsang Shiao
(74) *Attorney, Agent, or Firm* — Connolly Bove Lodge & Hutz LLP

(57) ABSTRACT

The present invention relates to a process for preparing an aminoalkyl nitrile by reaction of a corresponding monoamine with a corresponding alkenyl nitrile in a continuous mode of operation, which comprises the steps (a) introduction of the corresponding monoamine into a continuously conveyed reaction stream;
(b) introduction of the corresponding alkenyl nitrite into the reaction stream, with this already comprising the aminoalkyl nitrile on addition;
(c) reaction of the reaction stream in a first reaction region; and
(d) at least partial transfer of the reaction stream into at least one second reaction region for further reaction.

Figure 1:
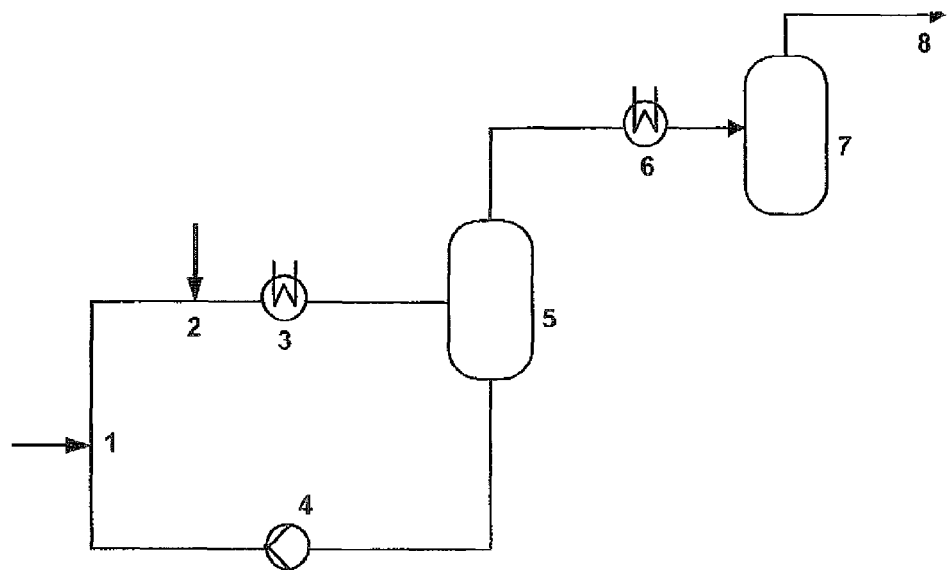

The invention further relates to a process for preparing a diamine from the aminoalkyl nitrile, suitable apparatuses for carrying out the processes and their corresponding use.

16 Claims, 1 Drawing Sheet

PROCESS FOR PREPARING AMINOALKYLNITRILES AND DIAMINES FROM SUCH NITRILES

CROSS REFERENCE TO RELATED APPLICATIONS

This application is a 35 U.S.C. 371 National Stage Application of International Application No. PCT/EP2007/054381, filed May 7, 2007, claiming priority from European Application No. 06113718.8, filed May 9, 2006, the entire contents of which are incorporated herein by reference in their entireties.

The present invention relates to a process for preparing an aminoalkyl nitrite by reaction of a corresponding monoamine with a corresponding alkenyl nitrile and also a process for preparing a diamine from such an aminoalkyl nitrite, and also apparatuses which can be used for carrying out the processes.

Diamines are an important group of chemicals which are used in a wide variety of ways as starting materials, intermediates or end products.

3-Dimethylaminopropylamine (DMAPA, N,N-dimethyl-1,3-diaminopropane), in particular, is an important intermediate for the industrial production of, for example, liquid soaps. In addition, DMAPA serves as starting material for the preparation of coagulants and is even said to have anticorrosive properties.

Diamines, like their amine analogues, are frequently prepared by reduction of nitriles. This reaction is particularly advantageous when primary amines are to be obtained.

The corresponding nitriles, which may already have an amino function, are obtained, for example, from alkenyl nitriles by addition of a monoamine onto the C—C double bond.

It is particularly advantageous if an integrated production process or an integrated apparatus can be used for the preparation of diamines from nitrites. Here, the product stream obtained first, which comprises the amino nitrites is used directly or after purification for conversion into the diamine in a further step.

Here, the quality of the aminoalkyl nitrile product stream from the first reaction (monoamine and alkenyl nitrite) is of critical importance for the reduction reaction of the nitrite, especially for the consumption of the catalyst used in the reduction.

In the case of 3-dimethylaminopropylamine, the preparation of 3-dimethylaminopropionitrile (DMAPN) is therefore important, with the latter being prepared from acrylonitrile and dimethylamine. The literature describes integrated processes, in particular for preparing DMAPA, which comprise both the addition step and the reduction step. Furthermore, optimized processes are described for each of the individual steps.

These processes can be divided firstly into processes which are carried out batchwise or at least semibatchwise and processes which can be carried out in a continuous mode of operation.

An integrated production process by means of which, for example, DMAPA can be prepared batchwise is described in the German patent application having the application number 10 2005 052 457.5, which was filed by the applicant.

However, it has been found to be advantageous to provide continuous processes as an alternative to such at least partly batchwise processes. Here, it is particularly important to provide a process for the first step which is optimized for the second (reduction) step so that optimized diamine production is likewise obtained in the second (reduction) step.

In this context, a high degree of optimization means, in particular, that a high individual or total yield of diamine is achieved. In addition, it is important for the yield to be achieved with a very high individual or total conversion. Furthermore, another quality criterion is the space-time yields with which such a process can be carried out. Finally, the consumption of the catalyst used in the reduction also plays an important role.

A process for preparing 3-dimethylaminoproprionitrile is described, for example, in DD-A 58 306. In this, it is proposed that previously formed 3-dimethylaminopropionitrile be used as solvent and diluent in the reaction of acrylonitrile with dimethylamine in order to achieve, owing to the exothermic reaction and the boiling behavior of dimethylamine, a required improved heat distribution and removal. This is said to increase the yield of 3-dimethylaminopropionitrile.

DD-A 222 011 describes a process for the continuous preparation of DMAPN, in which the reaction components are, in the liquid state, firstly placed in a mixing chamber in a tube reactor and then mixed stepwise and reacted stepwise over the total length of the reactor.

Finally, DE-A 27 09 966 describes the preparation of DMAPN, but in this the dimethylamine is used in gaseous form and the reaction is carried out in a bubble column reactor in which the reactants are conveyed in countercurrent.

Although optimized processes are known in the prior art, there is still a need to provide further processes and corresponding apparatuses in order to optimize the preparation of an aminoalkyl nitrile and/or the resulting preparation of a diamine.

It is therefore an object of the present invention to provide processes and apparatuses which allow such optimization.

The object is achieved by a process for preparing an aminoalkyl nitrile by reaction of a corresponding monoamine with a corresponding alkenyl nitrile in a continuous mode of operation, which comprises the steps (a) introduction of the corresponding monoamine into a continuously conveyed reaction stream;
(b) introduction of the corresponding alkenyl nitrile into the reaction stream, with this already comprising the aminoalkyl nitrile on addition;
(c) reaction of the reaction stream in a first reaction region; and
(d) at least partial transfer of the reaction stream into at least one second reaction region for further reaction.

It has been found that it is advantageous, especially in the continuous mode of operation, not to add the alkenyl nitrile to pure monoamine and, in addition, to separate the reaction regions so that the reaction can be carried out in at least two stages.

The above-described optimized process has the further advantage that it is possible to obtain an aminoalkyl nitrile stream which is particularly suitable for use in the subsequent reduction of the nitrile to the corresponding diamine.

The process of the invention for preparing an aminoalkyl nitrile is thus based on the addition reaction in which a primary or secondary monoamine is added onto the C—C double bond of an alkenyl nitrile.

For the purposes of the present invention, the terms "corresponding alkenyl nitrile" and "corresponding monoamine" mean that these are selected so that the aminoalkyl nitrile having the desired structural formula is obtained after the above-described synthesis step.

For example, if the alkenyl nitrile is acrylonitrile (ACN) and the monoamine is dimethylamine (DMA), reaction of the starting materials gives the desired 3-dimethylaminopropionitrile (DMAPN). In other words, if DMAPN is to be obtained in the process of the invention, it can clearly be seen that the corresponding alkenyl nitrile is ACN and the corresponding monoamine is DMA.

The alkenyl nitrite is preferably a $C_2$-$C_4$-alkene which can be linear or branched and in which a hydrogen atom has been replaced by the cyano group.

The term $C_2$-$C_4$-alkene refers to an alkene which has from 2 to 4 carbon atoms and comprises at least one C—C double bond. Preference is given to precisely one C—C double bond being present in the α,β position relative to the cyano group. Examples of $C_2$-$C_4$-alkenes are ethene, propene, 1-butene, 2-butene, 2-methylpropene.

Examples of alkenyl nitrites are acrylonitrile, but-2-enenitrile, methacrylonitrile, pent-2-enenitrile, 2-ethylacrylonitrile, 2-methylbut-2-enenitrile and 3-methylbut-2-enenitrile.

Preference is given to ACN.

The monoamine is preferably a primary or secondary amine of the general formula $R^1R^2NH$, where $R^1$, $R^2$ are each, independently of one another, H or $C_1$-$C_4$-alkyl, with the proviso that at least one radical $R^1$, $R^2$ is not hydrogen.

$C_1$-$C_4$-Alkyl is methyl, ethyl, n-propyl, i-propyl, 1-n-butyl, 2-n-butyl, i-butyl, t-butyl.

Preference is given to DMA.

In a particularly preferred embodiment, the aminoalkyl nitrile is 3-dimethylaminopropionitrile.

The process of the invention for preparing the aminoalkyl nitrile should be carried out in a continuous mode of operation This makes particularly efficient conversion together with a high space-time yield possible.

Accordingly, in steps (a) and (b) of the process of the invention for preparing an aminoalkyl nitrile, the introduction of the corresponding monoamine and the introduction of the corresponding alkenyl nitrile is carried out into a continuously conveyed reaction stream. Here, care has been taken to ensure that the corresponding alkenyl nitrile is introduced into the reaction stream in such a way that this already comprises the aminoalkyl nitrile on addition. This ensures that the monoamine present in the reaction stream is, if appropriate, present in sufficient dilution for the heat of reaction evolved on addition of the alkenyl nitrile can be controlled appropriately. This can also be achieved by the reaction stream after introduction of the corresponding alkenyl nitrile being passed through a heat exchanger in order to be able, if appropriate, to remove heat. The actual reaction of the monoamine with the alkenyl nitrile occurs in a first reaction region. This first reaction region can be a zone in a reactor or a reactor as such.

A reaction region is typically distinguished from line regions which serve merely for introduction or discharge of the reaction stream by the residence time of the stream in the respective regions. The mean residence time in a reaction region is preferably more than 15 minutes, more preferably more than 30 minutes, with the mean residence time for line regions generally being less than 10 minutes.

Furthermore, at least partial transfer of the reaction stream into at least one second reaction region which is physically separate from the first reaction region occurs for the purposes of further reaction in the process of the invention for preparing an aminoalkyl nitrile. The second reaction region can be a further zone in the abovementioned reactor or be a further reactor or a reactor cascade. The physical separation of first and second reaction regions can be effected, for example, by means of pipes.

It is advantageous for the entire reaction stream not to be transferred into at least one second reaction region but instead part of the reaction stream which comprises aminoalkyl nitrile already formed to be recirculated in a recycle mode so that the corresponding monoamine and the corresponding alkenyl nitrile can each be introduced into the reaction stream comprising aminoalkyl nitrile after at least commencement of aminoalkyl nitrite formation in the first reaction region.

A preferred embodiment of the process of the invention for preparing an aminoalkyl nitrile therefore comprises carrying out at least the steps (a) to (c) of the process of the invention for preparing an aminoalkyl nitrite in the recycle mode.

Furthermore, it has been found to be advantageous for the corresponding monoamine and the corresponding alkenyl nitrite to be introduced in liquid form. This allows a higher conversion at a better space-time yield compared to processes in which the monoamine is introduced in the gaseous state into the reaction mixture. For this reason, the corresponding alkenyl nitrile and the corresponding monoamine are introduced at a suitable temperature and a suitable pressure which ensure that these starting materials are present in liquid form for the preparation of the aminoalkyl nitrile.

A preferred embodiment of the process of the invention for preparing an aminoalkyl nitrile therefore preferably involves introduction of the corresponding alkenyl nitrile and of the corresponding monoamine in liquid form.

Furthermore, it is preferred that, on addition of the corresponding alkenyl nitrile, the reaction stream has a minimum excess of corresponding monoamine of 0.1 mol % based on the alkenyl nitrite. Furthermore, the molar excess of monoamine based on the alkenyl nitrite has a value in the range from 0.1 to 20%. The value is more preferably in the range from 1 to 10 mol %. In particular, the value is in the range from 2 to 8 mol %.

The excess of monoamine based on the alkenyl nitrite can be achieved by addition of the two starting materials in the corresponding ratio if the introduction of the monoamine is effected physically before, in the direction of the reaction stream, the introduction of the alkenyl nitrite.

The reaction of the reaction stream or of the monoamine with the alkenyl nitrile in the reaction stream occurs in two different reaction regions. This has the advantage that different reaction conditions can be selected for the reaction. In this way, more complete reaction of the alkenyl nitrile can be achieved while simultaneously reducing the proportion of by-products in the reaction stream.

The reaction in step (c) of the process of the invention for preparing an aminoalkyl nitrite is preferably carried out so that the consumption of alkenyl nitrite in the first reaction region is from 80 to 98%. This means that the reaction stream has a first concentration of alkenyl nitrite on entering the first reaction region and has a second concentration after leaving the first reaction region which are such that 1 minus the ratio of the second concentration to the first concentration is from 0.8 to 0.98.

The conversion in the first reaction region is more preferably in the range from 90 to 95%.

Preference is also given to the residual content of alkenyl nitrite in the reaction stream after the reaction in step (d) of the process of the invention for preparing an aminoalkyl nitrile being less than 1% by weight.

In addition, further reaction regions can be present. In this case, it is sufficient for the last reaction region present in the direction of the reaction stream to be configured so that the abovementioned residual content of alkenyl nitrite in the reaction stream is less than 1% by weight.

When more than two reaction regions are present, the conversion in the first, in the direction of the reaction stream, reaction region can, if appropriate, be lower than that indicated above. As stated above, an advantage in the process of the invention for preparing an aminoalkyl nitrite is that the reaction to form alkenyl nitrite is carried out in two different reaction regions. As a result, it is possible to select different reaction conditions for the reaction. It has been found to be advantageous for the reaction stream in the first and second reaction regions in the reaction to have different temperatures. In particular, preference is given to the reaction stream in the first reaction region in the reaction having a higher temperature than in the at least second reaction region.

The temperature of the reaction stream in the first reaction region is preferably in the range from 20° C. to 110° C. The range is more preferably from 60° C. to 80° C. The temperature of the reaction stream in the at least second reaction region is preferably in the range from 0 to 100° C., in particular in the range from 30 to 60° C.

If at least one further reaction region is present, the different, preferably lower, temperature compared to the first reaction region can also be present only in the at least further reaction region.

In addition, the pressure in the first and second reaction regions can be different. However, the pressure can likewise be the same, which is preferred. A gauge pressure in the range from 1 bar to 20 bar preferably prevails in the first and second reaction regions. Preference is therefore given to the gauge pressure in the first and second reaction regions of the process of the invention for preparing an aminoalkyl nitrite being identical or different and being in the range from 1 bar to 20 bar. The gauge pressure is preferably from 2 to 5 bar. Preference is also given to the feed streams for the corresponding monoamine and the corresponding alkenyl nitrite having a gauge pressure which is just as high.

It is known that water added in the addition of a monoamine onto the C—C double bond of an alkenyl nitrite catalyzes the reaction. Preference is therefore also given to water being introduced into the reaction stream before the reaction in the first reaction region before the reaction stream reaches the first reaction region.

The water can, for example, be introduced into the reaction stream in the form of an additional feed stream. Furthermore, it is possible for at least part of the monoamine to be introduced in the form of an aqueous solution into the reaction stream. This can be effected, for example, in the form of a from 30 to 70% strength by weight aqueous monoamine solution. In addition, the alkenyl nitrite used can comprise water.

The process of the invention for preparing an aminoalkyl nitrile preferably comprises a further step (e) in which the reaction stream is discharged from the second reaction region after the reaction.

Furthermore, unreacted monoamine can be separated off from the reaction stream after the reaction in the second reaction region either in the second reaction region or outside the second reaction region. This can be effected, for example, by distillation. A further vessel, for example a distillation column, can be used for this purpose. Such a separation of the unreacted monoamine is preferably carried out outside the second reaction region, in particular downstream thereof. The monoamine which has been recovered in this way can be fed back into the reaction stream before it reaches the first reaction region. This recirculation can be complete or partial. It is likewise conceivable for the recovered unreacted monoamine to be processed further or disposed of.

The present invention further provides a process for preparing a diamine from a corresponding aminoalkyl nitrite, which comprises the steps:

(a) introduction of the reaction stream discharged in step (e) of the process of the invention for preparing an aminoalkyl nitrite into a reduction region; and (b) reduction of the aminoalkyl nitrite present in the reaction stream to the corresponding diamine.

Based on the reaction stream as is obtained from the process of the invention for preparing an aminoalkyl nitrite after at least 2-stage reaction, the present invention further provides the reduction of the corresponding aminoalkyl nitrile to the diamine. Here, the nitrite group is thus converted, in a second reaction step, into the oxidation state of an amine. The product obtained in this way comprises not only this amino function but also a further amino function which was introduced by means of the monoamine.

In a preferred embodiment, the reduction is effected by means of hydrogen. This can be used as such or as part of a gas mixture. The nitrite group of the aminoalkyl nitrile is in this way converted into a primary amine function.

Ammonia can be introduced into the reaction stream before step (b) of the process of the invention for preparing a diamine.

Steps (a) and (b) of the process of the invention for preparing a diamine are preferably carried out in a continuous mode of operation.

Particular preference is given to recirculating at least part of the crude product formed after the reduction in step (b) so as to form a recycle stream.

When such a recycle stream is present, preference is given to hydrogen and ammonia being used and being introduced into the recycle stream before the reaction stream discharged from the first step is introduced into the recycle stream.

It is very particularly preferred for the recycle stream to go through a heat exchanger which heats the recycle stream after introduction of ammonia and hydrogen and before introduction of the reaction stream discharged from the first step.

The molar ratio of ammonia to aminoalkyl nitrile is, for example, about 5. When hydrogen is used for the hydrogenation, a total pressure in the range from 50 to 300 bar can be set. The total pressure is the sum of the partial pressures of ammonia, aminoalkyl nitrile, hydrogen and, if appropriate, unreacted starting materials and products formed and also possibly water at the respective temperature and is advantageously set to the desired value by injection of hydrogen. In a preferred embodiment, steps (a) and (b) of the process of the invention for preparing the diamine are carried out in a continuous mode of operation.

A catalyst is advantageously employed, particularly when hydrogen is used. The reduction preferably takes place on a fixed bed of catalyst. Upflow mode operation or downflow mode operation is possible here. Suitable catalysts for the hydrogenation of the aminoalkyl nitrile to the corresponding diamine are described in EP-B 742 045 or EP-B 892 77. The maximum temperature in the reduction region during the reduction is preferably 150° C.

As catalysts for the hydrogenation of the nitrile function to the amine, it is possible to use, in particular, catalysts which comprise, as active species, one or more elements of transition group 8 of the Periodic Table (Fe, Co, Ni, Ru, Rh, Pd, Os, Ir, Pt), preferably Fe, Co, Ni, Ru or Rh, particularly preferably Co or Ni. These include skeletal catalysts (also referred to as Raney® type, hereinafter also: Raney catalyst) which are obtained by leaching (activation) of an alloy of a hydrogenation-active metal and a further component (preferably Al). The catalysts can additionally comprise one or more promoters.

The catalysts can be used as all-active catalysts or in supported form. Supports used are preferably metal oxides such as $Al_2O_3$, $SiO_2$, $ZrO_2$, $TiO_2$, mixtures of metal oxides or carbon (activated carbon, carbon black, graphite).

Before use, the oxidic catalysts are activated outside the reactor or in the reactor by reduction of the active metal oxides in a hydrogen-comprising gas stream at elevated temperature. If the catalysts are reduced outside the reactor, passivation by means of an oxygen-comprising gas stream or embedding in an inert material can then be carried out in order to avoid uncontrolled oxidation in air and make safe handling possible.

Particularly preferred fixed-bed catalysts are the all-active cobalt catalysts doped with Mn, P and alkali metal (Li, Na, K, Rb, Cs) which are disclosed in EP-A 1 742 045. The catalytically active composition of these catalysts comprises, before reduction with hydrogen, from 55 to 98% by weight, in particular from 75 to 95% by weight, of cobalt, from 0.2 to 15% by weight of phosphorus, from 0.2 to 15% by weight of manganese and from 0.05 to 5% by weight of alkali metal, in particular sodium, in each case calculated as oxide.

Further suitable catalysts are the catalysts disclosed in EP-A 963 975, which, before the treatment with hydrogen, comprise from 22 to 40% by weight of $ZrO_2$, from 1 to 30% by weight of oxygen-comprising compounds of copper, calculated as CuO, from 15 to 50% by weight of oxygen-comprising compounds of nickel, calculated as NiO, with the molar Ni:Cu ratio being greater than 1, from 15 to 50% by weight of oxygen-comprising compounds of cobalt, calculated as CoO, from 0 to 10% by weight of oxygen-comprising compounds of aluminum and/or manganese, calculated as $Al_2O_3$ or $MnO_2$, and no oxygen-comprising compounds of molybdenum; for example the catalyst A disclosed in this document which has the composition 33% by weight of Zr, calculated as $ZrO_2$, 28% by weight of Ni, calculated as NiO, 11% by weight of Cu, calculated as CuO and 28% by weight of Co, calculated as CoO.

Also suitable are the catalysts disclosed in EP-A 696 572, which, before reduction with hydrogen, comprise from 20 to 85% by weight of $ZrO_2$, from 1 to 30% by weight of oxygen-comprising compounds of copper, calculated as CuO, from 30 to 70% by weight of oxygen-comprising compounds of nickel, calculated as NiO, from 0.1 to 5% by weight of oxygen-comprising compounds of molybdenum, calculated as $MoO_3$, and from 0 to 10% by weight of oxygen-comprising compounds of aluminum and/or manganese, calculated as $Al_2O_3$ or $MnO_2$. Mention may be made by way of example of the catalyst specifically disclosed in this document which has the composition 31.5% by weight of $ZrO_2$, 50% by weight of NiO, 17% by weight of CuO and 1.5% by weight of $MoO_3$. Likewise suitable are the catalysts described in WO-A 99/44984 which comprise (a) iron or a compound based on iron or mixtures thereof, (b) from 0.001 to 0.3% by weight, based on (a), of a promoter based on 2, 3, 4 or 5 elements selected from the group consisting of Al, Si, Zr, Ti, V, (c) from 0 to 0.3% by weight, based on (a), of a compound based on an alkali metal and/or alkaline earth metal and (d) from 0.001 to 1% by weight, based on (a), of manganese.

The reduction can be carried out adiabatically if the way in which the reaction is carried out is appropriate.

The stream obtained from the reduction comprises not only the product but also ammonia and hydrogen which can, if appropriate, be recirculated after having been separated off.

The invention further provides an apparatus for preparing an aminoalkyl nitrile by reaction of a corresponding monoamine with a corresponding alkenyl nitrile in a continuous mode of operation, which comprises a first reaction region comprising
    an inlet provided with a feed line, with the feed line having
        a first inlet which is suitable for introducing the monoamine into the feed line;
        a second inlet which is suitable for introducing the alkenyl nitrile into the feed line and is located between the first inlet and the inlet of the first reaction region;
    an outlet which is connected to the feed line; and
    a transfer facility to a second reaction region; and
a second reaction region,
with the feed line comprising the aminoalkyl nitrile.

The above-described apparatus for preparing an aminoalkyl nitrile is a preferred apparatus for carrying out the process of the invention for preparing an aminoalkyl nitrile.

The apparatus comprises a first reaction region which comprises an inlet provided with a feed line, with the feed line having a first inlet which is suitable for introducing the monoamine into the feed line and a second inlet which is suitable for introducing the alkenyl nitrile into the feed line. The second inlet is located between the first inlet and the inlet of the first reaction region. Furthermore, the first reaction region has an outlet which is connected to the feed line. This enables the process of the invention for preparing an aminoalkyl nitrile to be carried out in a continuous recycle mode or the apparatus of the invention for preparing an aminoalkyl nitrile to be operated. Finally, the first reaction region has a transfer facility leading to a second reaction region. Accordingly, the apparatus of the invention for preparing an aminoalkyl nitrile likewise has a second reaction region. The apparatus of the invention for preparing an aminoalkyl nitrile comprises the aminoalkyl nitrile in the feed line.

The latter ensures that when the alkenyl nitrile is introduced via the second inlet it is diluted by the aminoalkyl nitrile and no introduction of the alkenyl nitrile into pure monoamine thus occurs.

The first and second reaction regions of the apparatus of the invention for preparing an aminoalkyl nitrile can be present in the form of different zones in one reactor vessel. However, preference is given to the first and second reaction regions being different reactor vessels or a cascade of vessels.

These two reactor vessels can be connected to one another by means of a pipe.

In addition, the present invention further provides an apparatus for preparing a diamine from a corresponding aminoalkyl nitrile, which comprises an apparatus for preparing an aminoalkyl nitrile as described above; and
a reduction region.

The reduction region is preferably a fixed-bed reactor.

As stated above, the apparatus of the invention for preparing an aminoalkyl nitrile is a preferred apparatus for carrying out a process according to the invention for preparing an aminoalkyl nitrile.

The present invention therefore further provides for the use of an apparatus according to the invention for preparing an aminoalkyl nitrile by reaction of a corresponding monoamine with a corresponding alkenyl nitrile in a continuous mode of operation.

In addition, the apparatus of the invention for preparing a diamine is suitable for carrying out the process of the invention for preparing a diamine.

Accordingly, the invention further provides for the use of an apparatus according to the invention for preparing a diamine from a corresponding aminoalkyl nitrile. The invention is illustrated by the following figures and examples.

Figure 2:
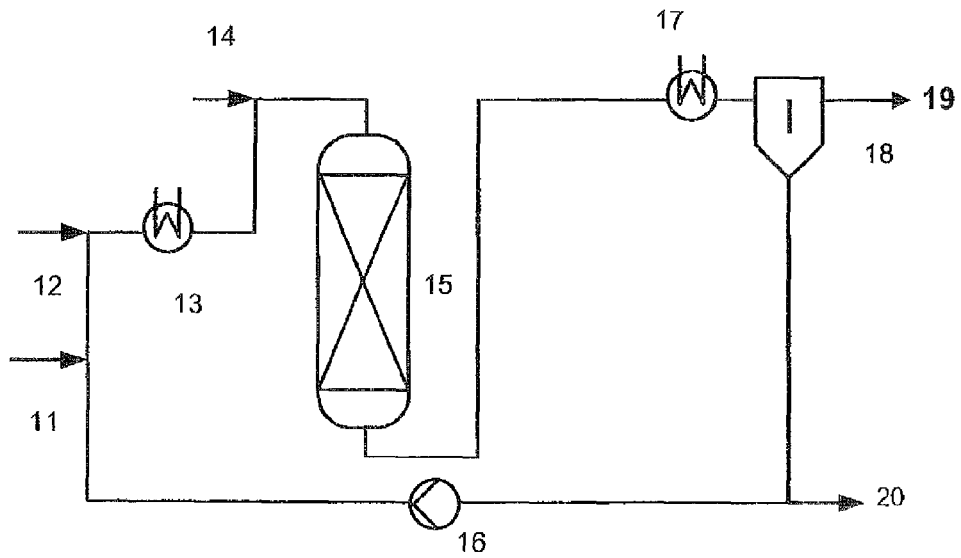

In the figures,

FIG. 1 shows a schematic flow diagram for an illustrative process for preparing an aminoalkyl nitrite according to the present invention and FIG. 2 shows a schematic flow diagram for the preparation of a diamine from a corresponding aminoalkyl nitrite according to the present invention.

FIG. 1 shows the step of reaction of the monoamine with alkenyl nitrite to form the corresponding aminoalkyl nitrite. Here, in a recycle mode of operation, the monoamine is introduced via inlet 1 and the alkenyl nitrite is introduced via inlet 2 into the recycle stream. The actual reaction of the monoamine with the alkenyl nitrile occurs in the reactor 5 via a pipe which provides a heat exchanger 3 between inlet 2 and reactor 5. The reaction stream present in reactor 5 is partly recirculated by means of a pump 4 into the recycle stream and the uncirculated part of the reaction stream is transferred via a heat exchanger 6 into a second reactor 7. This allows the reaction stream in the reactors 5 and 7 to have different temperatures. The reaction stream comprising aminoalkyl nitrite leaves the reactor 7 via outlet 8.

FIG. 2 shows the reduction step with the aid of hydrogen. The aminoalkyl nitrite coming from outlet 8 is transferred via inlet 14 into a fixed-bed reactor 15 by means of a pipe. Here, the fixed bed of catalyst brings about the reduction of the nitrile group by means of hydrogen. This is introduced via inlet 12. Ammonia is introduced via inlet 11, and the reaction stream is conveyed in such a way that it passes through a heat exchanger 13 after addition of hydrogen and ammonia in order to heat it before the aminoalkyl nitrite enters the reactor 15 via inlet 14. This has, in particular, the advantage that the aminoalkyl nitrite is reacted very rapidly in the reactor 15 and therefore has only a very short residence time before it comes into contact with the hydrogenation catalyst. This results in less by-product (bisdiamine) being formed. The reaction stream flows through the fixed-bed reactor 15 from the top downward (downflow mode) and travels via the heat exchanger 17 to the separator 18 in which the crude product is separated off from hydrogen, monoamine and ammonia and can be discharged via the outlet 20. In addition, at least part of the crude product can be recirculated to the reaction stream by means of the pump 16. At least partial recirculation results in a recycle process in the hydrogenation, too, which is preferred. The mixture of hydrogen, monoamine and ammonia which is obtained can be discharged via outlet 19.

EXAMPLES

Example 1

The addition of DMA onto ACN is carried out in a continuously operated cascade of stirred vessels, comprising three stirred vessels. The volume ratio of the three stirred vessels is 1:1.5:2.5. The reaction is carried out at a pressure of 5 bar.

The temperature in the first two stirred vessels is 60° C., and that in the third vessel is 30° C. The addition reaction is carried out at a throughput, calculated as acrylonitrile feed per unit time, based on the volume of the first stirred vessel, of 0.54 kg/l/h. The molar starting material ratio of DMA to ACN is 0.98. The residual acrylonitrile content is 3% by weight (based on the total reaction product mixture). The mean residence time of the reaction mixture in the vessels of the addition reaction stage is about 4 hours.

The reaction product mixture from the addition reaction stage is continuously hydrogenated over a cobalt-comprising fixed-bed catalyst in a continuously operated reactor in a second reaction stage. The space velocity over the catalyst is 1.0 kg(DMAPN crude output)/kg(catalyst)/h. The hydrogenation is carried out at an absolute pressure of 180 bar. The reactor outlet temperature is 120° C. The mass ratio of circulation stream to DMAPN feed is 2.5 kg/kg. The proportion of ammonia in the feed to the reaction is 0.8 kg (ammonia)/kg (DMAPN), and the molar ratio of ammonia to nitrile is 5.

After a total period of operation of 1300 h, an appreciable nitrile breakthrough is found in the hydrogenation (>0.1% of DMAPN in the output).

Example 2

The addition of DMA onto ACN is carried out in a continuously operated cascade of stirred vessels, comprising seven stirred vessels. The volume ratio of the seven stirred vessels is 1:1.5:2.5:3.4:3.4:3.4:3.4. The reaction is carried out at a pressure of 5 bar.

The temperature in the first two stirred vessels is 60° C., and that in the third to seventh vessels is 40° C. The addition reaction is carried out at a throughput, calculated as acrylonitrile feed per unit time, based on the volume of the first stirred vessel, of 0.54 kg/l/h. The molar starting material ratio of DMA to ACN is 0.98. The residual acrylonitrile content is about 2% by weight (based on the total reaction product mixture). The mean residence time of the reaction mixture in the vessels of the addition reaction stage is about 16 hours.

After a period of operation of 500 h a reduced amount of DMA is added to the addition reactor for about 24 h, which leads to the residual acrylonitrile content in the product mixture rising to 5 to 30% by weight.

The reaction product mixture from the addition reaction stage is continuously hydrogenated over a cobalt-comprising fixed-bed catalyst in a continuously operated reactor in a second reaction stage. The space velocity over the catalyst is 1.0 kg(DMAPN crude output)/kg(catalyst)/h. The hydrogenation is carried out at an absolute pressure of 180 bar. The reactor outlet temperature is 120° C. The mass ratio of circulation stream to DMAPN feed is 2.5 kg/kg. The proportion of ammonia in the feed to the reaction is 0.8 kg (ammonia)/kg (DMAPN), and the molar ratio of ammonia to nitrile is 5.

No nitrile breakthrough is detected in the output from the hydrogenation stage within the first 500 h of operation.

After a total period of operation of 530 h, an appreciable nitrile breakthrough is found in the hydrogenation (>0.2% of DMAPN in the output).

Example 3

The addition of DMA onto ACN is carried out in a continuously operated cascade of stirred vessels, comprising three stirred vessels. The volume ratio of the three stirred vessels is 1:1.5:2.5. The reaction is carried out at a pressure of 5 bar.

The temperature in the first two stirred vessels is 60-80° C., and that in the third vessel is 30-45° C. The addition reaction is carried out at a throughput, calculated as acrylonitrile feed per unit time, based on the volume of the first stirred vessel, of 0.44-0.54 kg/l/h. The molar starting material ratio of DMA to ACN is 1.08-1.18. The residual acrylonitrile content is less than 0.2% by weight (based on the total reaction product mixture). The mean residence time of the reaction mixture in the vessels of the addition reaction stage is about 4 hours.

The reaction product mixture from the addition reaction stage is continuously hydrogenated over a cobalt-comprising fixed-bed catalyst in a continuously operated reactor in a second reaction stage. The space velocity over the catalyst is 1.0 kg(DMAPN crude output)/kg(catalyst)/h. The hydrogenation is carried out at an absolute pressure of 180 bar. The reactor outlet temperature is 120° C. The mass ratio of circulation stream to DMAPN feed is 2.5 kg/kg. The proportion of ammonia in the feed to the reaction is 0.8 kg (ammonia)/kg (DMAPN), and the molar ratio of ammonia to nitrile is 5.

No nitrile breakthrough in the hydrogenation is found within a period of operation of 600 h.

Example 4

The addition reaction of DMA onto ACN is carried out in a continuously operated plant comprising a pumped circuit having two vessels and a vessel through which laminar flow occurs and two further vessels. The volume ratio of the vessels of the pumped circuit to the vessel through which laminar flow occurs and the two further vessels is 1:0.2:2.3.

The temperature in the pumped circuit is 60° C., and that in the further vessels is 30-45° C. The addition reaction is carried out at a throughput, calculated as acrylonitrile feed per unit time, based on the volume of the pumped circuit, of 0.75 kg/l/h. The ratio of the amount of crude DMAPN pumped through the first two vessels to reaction product mixture is 30 kg/kg.

The molar starting material ratio of DMA to ACN is 1.08. The residual acrylonitrile content is less than 0.1% by weight (based on the total reaction product mixture) in the reaction stream after the 5th vessel. The mean residence time of the reaction mixture in the vessels of the addition reaction stage is about 4 hours. The reaction is carried out at a pressure of 4 bar. The acrylonitrile used has a water content of about 0.4%.

The reaction product mixtures from the addition reaction stage are continuously hydrogenated over a cobalt-comprising fixed-bed catalyst in a continuously operated reactor in a second reaction stage. The space velocity is on average 1.0 kg (DMAPN crude output)/kg(catalyst)/h. The hydrogenation is carried out at an absolute pressure of 180 bar. The reactor outlet temperature is about 144° C. The mass ratio of circulation stream to DMAPN feed is 2.5 kg/kg. The proportion of ammonia in the feed to the reaction is 0.8 kg (ammonia)/kg (DMAPN), and the molar ratio of ammonia to nitrile is 5.

No nitrile breakthrough in the hydrogenation is found within a period of operation of 6 months; during this time, a total amount of about 4500 kg (DMAPN)/kg(catalyst) is hydrogenated.

The invention claimed is:

1. A process for preparing an aminoalkyl nitrile by reaction of a corresponding monoamine with a corresponding alkenyl nitrile in a continuous mode of operation, which comprises the steps
   (a) introduction of the corresponding monoamine into a continuously conveyed reaction stream;
   (b) introduction of the corresponding alkenyl nitrile into the reaction stream, with this already comprising the aminoalkyl nitrile on addition;
   (c) reaction of the reaction stream in a first reaction region; and
   (d) at least partial transfer of the reaction stream into at least one second reaction region for further reaction.

2. The process according to claim 1, wherein the aminoalkyl nitrile is 3-dimethylaminopropionitrile.

3. The process according to claim 1, wherein at least the steps (a) to (c) are carried out in the recycle mode.

4. The process according to claim 1, wherein the alkenyl nitrile and the monoamine are introduced in liquid form.

5. The process according to claim 1, wherein, on addition of the corresponding alkenyl nitrile, the reaction stream has a minimum excess of corresponding monoamine of 0.1 mol % based on the alkenyl nitrile.

6. The process according to claim 1, wherein the reaction in step (c) is carried out so that the consumption of alkenyl nitrile is in the range from 80 to 98%.

7. The process according to claim 1, wherein the residual content of alkenyl nitrile in the reaction stream after the reaction in step (d) is less than 1% by weight.

8. The process according to claim 1, wherein the reaction stream in the first and second reaction regions in the reaction have different temperatures.

9. The process according to claim 1, wherein the reaction stream in the first reaction region in the reaction has a higher temperature than in the at least second reaction region.

10. The process according to claim 1, wherein the temperature of the reaction stream in the first reaction region is in the range from 20° C. to 110° C.

11. The process according to claim 1, wherein the temperature of the reaction stream in the at least second reaction region is in the range from 0 to 100° C.

12. The process according to claim 1, wherein the gauge pressure in the first and second reaction regions is identical or different and is in the range from 1 bar to 20 bar.

13. The process according to claim 1, wherein water is introduced into the reaction stream before the reaction in the first reaction region.

14. The process according to claim 1, wherein the monoamine is introduced in the form of an aqueous solution into the reaction stream.

15. The process according to claim 1, wherein unreacted monoamine is separated off from the reaction stream after the reaction in the second reaction region either in or outside the second reaction region.

16. The process according to claim 1 which comprises the further step (e) discharge of the reaction stream from the second reaction region after the reaction.

* * * * *